United States Patent
Basped et al.

(10) Patent No.: US 7,522,972 B1
(45) Date of Patent: Apr. 21, 2009

(54) OXYGEN VENDING MACHINE

(76) Inventors: Beauford Basped, 4012 S. Freeway, Fort Worth, TX (US) 76110; Richard Lister, 1933 Lavaca Trail, Carrollton, TX (US) 75010

(*) Notice: Subject to any disclaimer, the term of this patent is extended or adjusted under 35 U.S.C. 154(b) by 722 days.

(21) Appl. No.: 11/149,765

(22) Filed: Jun. 10, 2005

(51) Int. Cl.
*G06F 17/00* (2006.01)

(52) U.S. Cl. .................. 700/232; 700/231; 700/237; 700/243; 222/3; 222/4; 128/200.24; 128/204.18

(58) Field of Classification Search ......... 700/231–244; 221/1–312 C; 222/3–6; 128/200.24, 204.18
See application file for complete search history.

(56) References Cited

U.S. PATENT DOCUMENTS

| | | | |
|---|---|---|---|
| 3,604,416 A * | 9/1971 | Petrahai et al. | 128/201.25 |
| 4,088,161 A | 5/1978 | Ikemoto | |
| 4,106,505 A | 8/1978 | Salter et al. | |
| 4,243,155 A * | 1/1981 | Stewart | 222/3 |
| 4,416,433 A | 11/1983 | Bellina | |
| 4,593,688 A * | 6/1986 | Payton | 128/200.28 |
| 4,628,194 A | 12/1986 | Dobbins et al. | |
| 4,648,888 A | 3/1987 | Rowland | |
| 4,778,042 A | 10/1988 | Warren et al. | |
| 4,822,384 A | 4/1989 | Kato et al. | |
| 5,134,541 A * | 7/1992 | Frouin | 361/622 |
| 5,370,161 A | 12/1994 | Shafer | |
| 5,381,019 A | 1/1995 | Sato | |
| 5,405,249 A | 4/1995 | Benson | |
| 5,578,115 A | 11/1996 | Cole | |
| 5,651,402 A | 7/1997 | McCaul | |
| 5,688,306 A | 11/1997 | Verini | |
| 5,839,434 A | 11/1998 | Enterline | |
| 6,536,431 B1 * | 3/2003 | Simler | 128/205.12 |
| 6,866,041 B2 * | 3/2005 | Hardy et al. | 128/204.18 |

* cited by examiner

*Primary Examiner*—Gene Crawford
*Assistant Examiner*—Michael K Collins
(74) *Attorney, Agent, or Firm*—Jack A. Kanz

(57) ABSTRACT

An oxygen vending machine receives payment from a user. The payment is validated for appropriateness and sufficiency. If a valid payment is made, then concentrated oxygen is provided to a nipple or coupling located in an accessible place. In addition, a packaged breathing device, such as a nasal cannula, is dispensed. The user retrieves the packaged nasal device and uses it to direct the concentrated oxygen from the nipple into the user's nose or mouth. The user may select the particular breathing device which is to be dispensed. The flow of concentrated oxygen to the nipple is ceased after a predetermined period of time has passed.

2 Claims, 2 Drawing Sheets

OXYGEN VENDING MACHINE

FIELD OF THE INVENTION

The present invention relates to a method and apparatus for vending oxygen for consumption by human beings.

BACKGROUND OF THE INVENTION

Altitude sickness can strike anyone who ascends from a relatively low altitude (for example sea level) to a relatively high altitude (for example 8,000 feet or more). Some visitors to the Rocky Mountains (as well as to other mountain ranges) suffer from altitude sickness. Symptoms of altitude sickness include headaches, dizziness, and shortness of breath.

The human body typically needs to acclimate to the lower oxygen levels of high altitudes. One way to obtain quick relief of altitude sickness is to breathe concentrated oxygen. This increases the level of oxygen in the blood.

Concentrated oxygen is available through medical services providers (ambulances, hospitals, etc.). Consequently, its use is restricted to those that also require medical assistance. There are however, situations where someone may wish to breathe concentrated oxygen without summoning medical assistance.

SUMMARY OF THE INVENTION

It is an object of the present invention to provide a method and apparatus for vending oxygen to human beings.

The present invention provides an apparatus for vending concentrated oxygen. The apparatus includes a source of concentrated oxygen, as well as a valve that is connected to an output of the source of concentrated oxygen. The valve is also connected to a coupling. A payment validator has an output. A timer is connected to the output of the payment validator. The timer is also connected to the valve. The valve is capable of being opened and closed by the timer. A dispenser of breathing devices is operable by the payment validator.

With the present invention, a human user makes a payment to the apparatus. The payment is validated and then concentrated oxygen is directed to a coupling. In addition, a breathing device is dispensed to the user. The user connects the breathing device to the coupling and begins to breathe oxygen.

In accordance with one aspect of the present invention, the source of concentrated oxygen is an oxygen concentrator.

In accordance with still another aspect of the present invention, the timer opens the valve for a predetermined period of time so as to deliver oxygen to the coupling.

In accordance with still another aspect of the present invention, the breathing devices are packaged nasal cannulas.

The present invention also provides a method for automatically vending concentrated oxygen. A source of concentrated oxygen is provided. A payment by a user is received and validated. If a valid payment is received, then the flow of concentrated oxygen is directed to a coupling for a predetermined period of time. In addition, a dispenser is operated in order to dispense a packaged breathing device. The breathing device is structured and arranged to be coupled to the coupling.

In accordance with one aspect of the method invention, the user is allowed to select a particular breathing device from the dispenser.

DESCRIPTION OF THE PREFERRED EMBODIMENT

Figure 1:
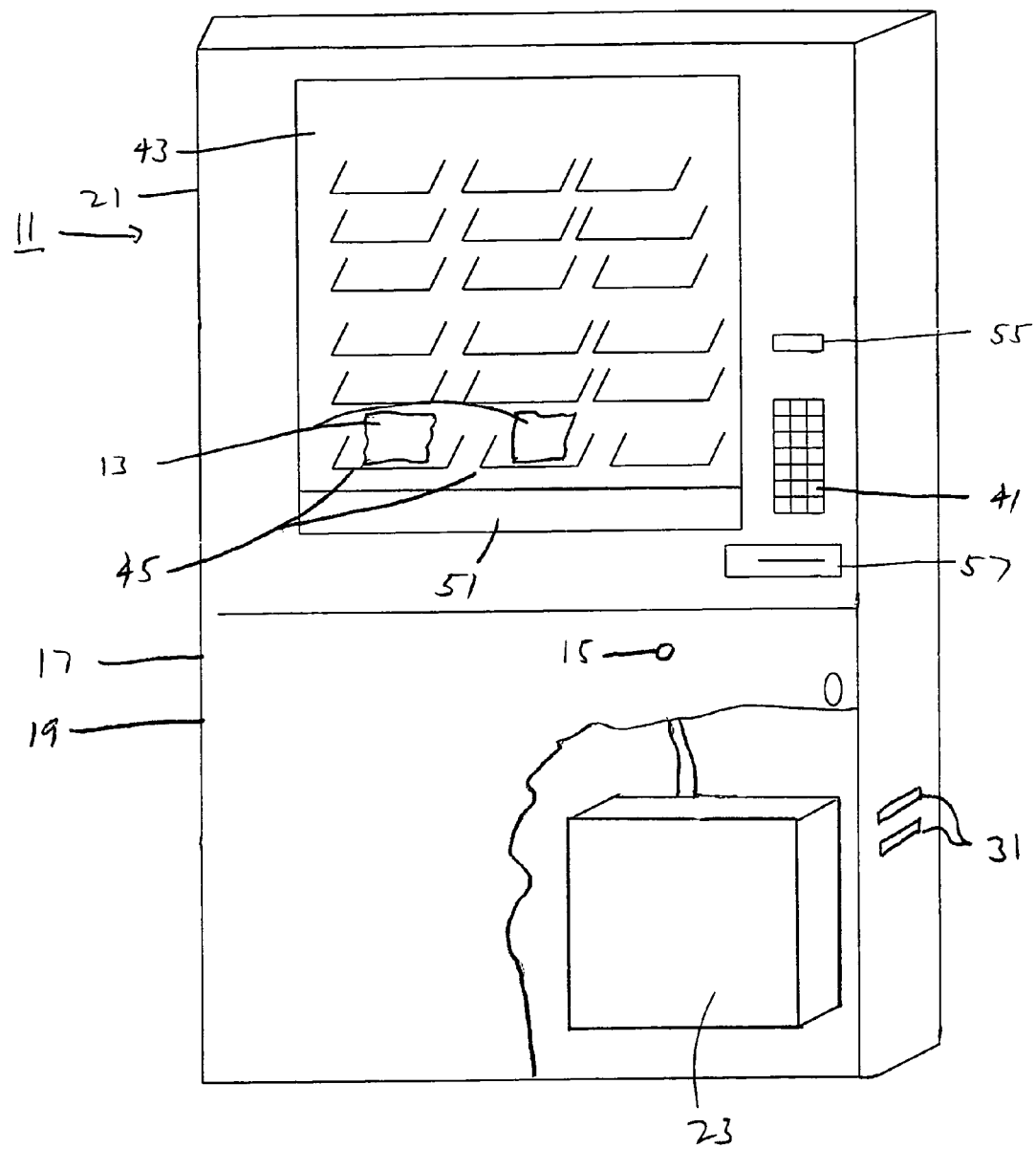
FIG. 1 is a schematic isometric view of the front of the machine of the present invention, shown partially cut away, in accordance with a preferred embodiment.

In FIG. 1, there is shown the oxygen vending machine 11 of the present invention, in accordance with a preferred embodiment. The oxygen vending machine 11 receives payment from a human user, whereupon a packaged breathing device 13 (such as a nasal cannula or mask) is dispensed. In addition, oxygen is provided to a coupling such as a nipple 15. The user connects the breathing device to the nipple and dons the breathing device so as to direct oxygen flow into the nose or mouth and then breathes normally. The restorative characteristics of oxygen can be felt by many after only a few moments of breathing. The user is apt to feel perkier, more energetic. After a period of time has passed, the flow of oxygen ceases. The user can disconnect the breathing device from the nipple or make another payment where additional oxygen is delivered through the breathing device.

The apparatus 11 will now be described in more detail. The apparatus 11 has a housing or cabinet 17. The housing has a lower portion 19, which contains the oxygen equipment, and an upper portion 21, which contains the breathing device dispensing equipment. Each of the lower and upper portions can be equipped with an access door.

Figure 2:
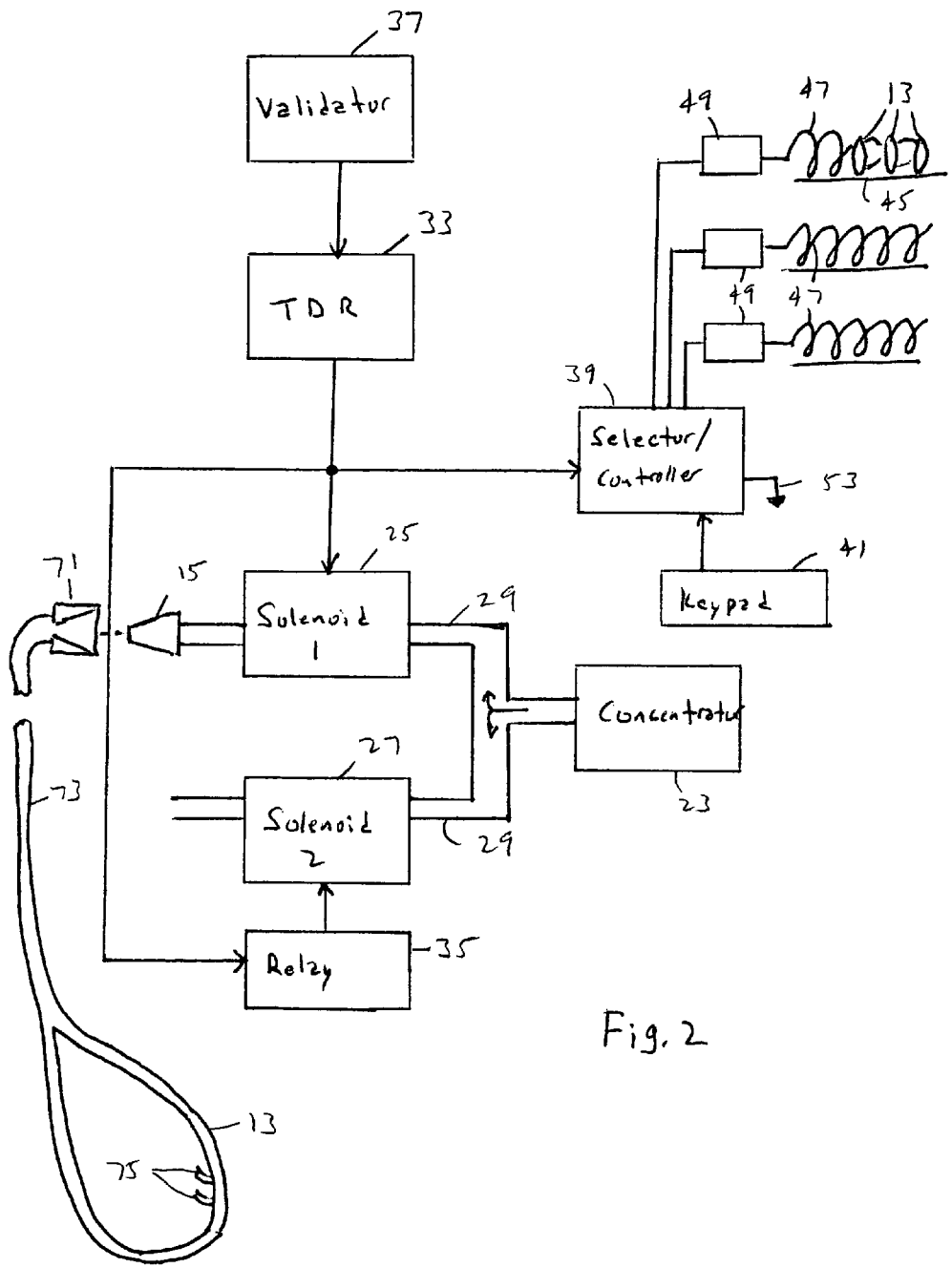
FIG. 2 is a block diagram of the electrical system of the machine.

As shown in FIGS. 1 and 2, the oxygen equipment includes an oxygen concentrator 23. The oxygen concentrator is a conventional, commercially available device. It is discussed in U.S. Pat. Nos. 2,944,627; 3,147,547; 3,280,536; 3,898,047; 4,822,384; and 5,578,115, the disclosures of which are incorporated herein by reference. In addition, U.S. Pat. No. 4,648,888 discloses oxygen concentrators.

The oxygen concentrator passes atmospheric air through a container of zeolite. The zeolite separates the nitrogen from the oxygen. The oxygen that is provided is concentrated and pressurized.

In the preferred embodiment, the oxygen concentrator 23 is continuously operated. It thus always produces concentrated oxygen, even when a user has not made a payment. The concentrated oxygen is diverted to and away from the nipple 15 that is located on the exterior of the cabinet 17 so as to be accessible by a user. Two solenoid valves 25, 27 are connected in parallel by hoses 29 with the oxygen output of the oxygen concentrator 23. The output of the first solenoid valve 25 is connected to the nipple 15 by way of a hose. The output of the second solenoid valve 27 is simply vented to the interior of the cabinet 17. The cabinet has vent openings 31 to allow atmospheric air to flow inside and into the concentrator.

The solenoid valves 25, 27 are operated by one or more relays. The first solenoid valve 25 is connected to the output of a time delay relay (TDR) 33. The TDR 33, which is conventional and commercially available, operates the first solenoid valve 25 for a programmed or predetermined period of time. The TDR 33 contains a dial that can be rotated to program the operational time from minutes to hours. In the preferred embodiment, the TDR 33 is programmed for 3-5 minutes, meaning that concentrated oxygen is provided to the nipple 15 for 3-5 minutes.

The output of the TDR 33 is also connected to another relay 35, which relay is connected to the second solenoid valve 27. The first and second solenoid valves 25, 27 operate in a flip-flop configuration: when the first solenoid valve 25 is open, concentrated oxygen flows to the nipple 15 and the second solenoid valve 27 is closed; when the second solenoid valve 27 is open, concentrated oxygen flows into the cabinet 17 and the first solenoid valve 25 is closed.

The TDR 33 is connected to a validator. The validator 37 is conventional and commercially available. See for example, U.S. Pat. Nos. 4,628,194 and 5,381,019, the specifications of which are incorporated herein by reference. The validator validates that a proper payment has been made. If so, then the validator operates the TDR 33. Payment can be made in a variety of ways. Coins can be used, as can paper money. A coin changer can be used in conjunction with the validator if payment by coins and/or paper money is accepted. The coin changer physically validates coins and/or paper money. Alternatively, payment can be made electronically such as by a magnetically encoded credit card or debit card. Payment can also be made by wireless devices such as a cellular telephone. If electronic payment is to be accepted, then access to a remote database is provided, such as through a cable or phone line.

The output of the TDR 33 is also connected to the dispensing equipment, located in the upper portion 21 of the cabinet. The dispensing equipment, which is conventional and commercially available, has a selector/controller 39 that is connected to the output of the TDR 33. The selector/controller 39 has a keypad 41 to allow a user to select which breathing device is to be dispensed. The upper portion 21 of the cabinet has a transparent window 43. The packaged breathing devices 13 are located on horizontal shelves 45 and are visible to a user through the transparent window 43. Helical coils 47 are oriented so that their longitudinal axes are parallel to the shelves and intersect the window 43. There is a space or gap between the ends of the coils 47 (and the shelves) and the transparent window 43 so that the packaged breathing devices 13 can be dispensed to the bottom of the upper portion 21 of the cabinet. There is a floor to the upper portion 21, which prevents the packaged breathing devices from entering the lower portion 19. The individual packages 13 are located in the spaces of the coils. The keypad 41 corresponds to the layout of the coils. For example, if there are two rows of coils, with four coils per row, then the keypad may designate the rows as A, B and the columns as 1, 2, 3 and 4. The coils 47 have a sign for identification purposes, which sign is typically located on the shelf below the coil and is visible through the transparent window 43. The sign displays the row and column designation to the user. The coil 47 is rotated by a stepping motor 49. The stepping motor 49 is controlled by the selector/controller 39 and, when activated, rotates the coil one revolution. A stepping motor 49 is provided for each individual coil 47.

The breathing devices are plastic, disposable items. In the preferred embodiment, the breathing devices are either nasal cannulas (see U.S. Pat. No. 4,106,505, the disclosure of which is incorporated herein by reference) or breathing masks. The breathing devices 13 have a fitting 71 that can be coupled to the nipple 15, a hose 73 and a gas delivery member 75. For a nasal cannula, the gas delivery member 75 are two stub hoses with orifices that are adapted to be partially inserted into the nostrils of a human. For a mask, the gas delivery member 75 is a face mask. The breathing devices are inexpensive and are meant to be thrown away after use. The breathing devices are contained within sealed plastic packages for sanitary purposes. A relatively long plastic hose extends from the cannula or mask. The free end of the hose has a fitting for coupling to the nipple 15.

The operation of the machine will now be described. The equipment inside the machine derives electrical power from an electrical wall outlet (for example 110V ac). As mentioned, the oxygen concentrator 43 operates continuously. A user approaches the machine and makes a payment, using coins, paper money, wireless devices, etc. Coins and paper are inserted into appropriate slots 55. The validator 37 checks the payment to determine if the appropriate tender has been made (that is are the coins and bills valid or counterfeit) and if the amount is correct (a money return 57 is also provided). Alternatively, if electronic payment is made, the validator accesses a remote database to check and make a record of the payment, or the validator may debit a debit card and access a remote database to record the debit and provide instructions to payment. If payment is invalid and/or insufficient then the TDR 33 is not operated. If payment is valid and sufficient, then the validator 37 operates the TDR 33.

When the TDR 33 is operated, it in turn opens the first solenoid valve 25 and closes the second solenoid valve 27 by way of the relay 35. This diverts the flow of concentrated oxygen from the concentrator 23 to the nipple 15. Before the validation of payment, concentrated oxygen from the concentrator 23 is merely vented into the interior of the lower portion 19 of the cabinet by way of the second solenoid valve 27.

The TDR 33 also energizes or activates the selector/controller 39. The user views the packaged breathing devices 13 through the window 43, decides which row and column to select and makes the selection using the keypad 41. Selector/controller 39 then operates the respective stepping motor 49 for the selected coil 47, and rotates the coil. As the coil 47 rotates, the packages 13 of breathing devices that are located inside that coil are advanced toward the window 43. The forwardmost package will drop off the shelf 45 and fall to the bottom of the upper portion 21, landing on the floor.

The user reaches a hand into the upper portion 21 through a swinging door 51, grabs the package and then retrieves the package through the door. The package is opened up and the breathing device 13 is withdrawn therefrom. The hose fitting is coupled to the nipple 15 (by simply pushing the fitting onto the nipple). Concentrated oxygen flows into the breathing device 13. The user puts on the breathing device so as to direct the concentrated oxygen into the nose or mouth or both. The volume of oxygen flow provided by the concentrator is relatively low, on the order of 1-5 liters per minute. Nasal cannulas are preferred over masks for delivering such low flows of oxygen.

After the predetermined period of time has elapsed, the TDR 33 closes the first solenoid valve 25 and opens the second solenoid valve 27. This once again directs the flow of concentrated oxygen away from the nipple 15 and into the interior of the cabinet 17. The flow of concentrated oxygen to the nipple 15 thus ceases. The user removes the breathing device from the face so as not to impede normal breathing.

The user can make another payment to obtain oxygen flow, without the dispensing of a breathing device. The use simply uses the previously dispensed breathing device, which can be reused by the same user. However, due to sanitary considerations, it is recommended that the breathing device not be used by another user. To obtain oxygen flow only, without the dispensing of a breathing device, the user makes the appropriate selection on the selector/controller 39. The appropriate selection for oxygen only is a null selection 53; because no breathing device is dispensed, no stepping motor 49 is operated. The amount of time that concentrated oxygen is provided to the nipple 15 is determined by the TDR 33.

Thus, a human user can pay for and breathe concentrated oxygen with the present invention. Although the present invention has been described as providing a source of concentrated oxygen by way of an oxygen concentrator, other sources can be utilized. For example, a pressurized tank or bottle of oxygen can be utilized. An advantage of the pressurized tank or bottle is that relatively high volumes of oxygen flows can be provided to the user, from 10-15 liters per minute. A mask may be a preferred over a nasal cannula for higher oxygen flows. If a pressurized tank or bottle is used, a regulator is also used to lower the pressure to a suitable level. The output of the regulator is connected to the first solenoid valve 25 that opens and closes to control the flow of oxygen from the tank or bottle.

Although the dispensing equipment has been described as being connected to the TDR, the dispensing equipment (namely the selector/controller) could be connected directly to the validator 37. Thus, the dispensing equipment need not be controlled by the TDR 33.

The foregoing disclosure and showings made in the drawings are merely illustrative of the principles of this invention and are not to be interpreted in a limiting sense.

The invention claimed is:

1. A method for automatically vending concentrated oxygen, comprising the steps of:
(a) providing a source of concentrated oxygen;
(b) receiving and validating payment by a user;
(c) if a valid payment is received, then directing flow of oxygen to a coupling for a predetermined period of time; and
(d) operating a dispenser to dispense a packaged breathing device, the breathing device being structured and arranged to be coupled to the coupling.

2. The method of claim 1 further comprising the step of allowing a user to select a particular device to be dispensed.

* * * * *